US006998422B2

(12) United States Patent
Ohsawa et al.

(10) Patent No.: US 6,998,422 B2
(45) Date of Patent: *Feb. 14, 2006

(54) LIPID PEROXIDE-LOWERING COMPOSITIONS

(75) Inventors: Tsuneki Ohsawa, Tokyo (JP); Ikuo Takagi, Matsudo (JP); Ippei Shimizu, Tokyo (JP); Tatsuhito Kondo, Tokyo (JP); Masato Nakayama, Saitama (JP); Yasuhiro Torizumi, Ryugasaki (JP)

(73) Assignee: Sankyo Company, Limited, Tokyo (JP)

( * ) Notice: Subject to any disclaimer, the term of this patent is extended or adjusted under 35 U.S.C. 154(b) by 256 days.

This patent is subject to a terminal disclaimer.

(21) Appl. No.: 10/428,394

(22) Filed: May 2, 2003

(65) Prior Publication Data

US 2003/0229124 A1 Dec. 11, 2003

Related U.S. Application Data

(63) Continuation-in-part of application No. PCT/JP01/09662, filed on Nov. 5, 2001.

(30) Foreign Application Priority Data

Dec. 18, 2000 (JP) .............................. 2000-383053

(51) Int. Cl.
*A61K 31/225* (2006.01)
*A61K 31/185* (2006.01)
*A61K 31/16* (2006.01)

(52) U.S. Cl. ...................... 514/548; 514/578; 514/616
(58) Field of Classification Search ................ 514/548, 514/356, 578, 616
See application file for complete search history.

(56) References Cited

U.S. PATENT DOCUMENTS

| 5,662,934 | A | 9/1997 | Najarian |
| 6,245,797 | B1 | 6/2001 | Winokur |
| 6,544,525 | B1 | 4/2003 | Yegorova |
| 2003/0220343 | A1 | 11/2003 | Ohsawa et al. |

FOREIGN PATENT DOCUMENTS

| GB | 2 077 264 A | 12/1981 |
| JP | 55-76816 A A | 6/1980 |
| JP | 58-69813 A A | 4/1983 |
| JP | 60/41611 A | 3/1985 |
| WO | 94/15592 A | 7/1994 |
| WO | 97/38694 A | 10/1997 |
| WO | 99/06035 X | 2/1999 |

OTHER PUBLICATIONS

STN Registry File Abstract, Registry No. 6556-11-2 "Inositol, hexanicotinate, myo-", copyright 2005 ACS on STN.*
Biosis Abstract, Accession No. 1972:156777, Richard, A, Therapie der Gegenwart, (1971), vol. 110, No. 11, pp. 1679-1687.*
Medline Abstract, Accession No. 81255317, Wechsler, et al., Artery (1980), 8(6), 519-29.*
Hcaplus Abstract, Accession No. 122:129709, Deslypere, Journal of Internal Medicine, Supplement (1994), 236(736), 69-74.*
Medline Abstract, Accession No. 8937733, Mitani et al., British Journal of Pharmacology, (Nov. 1996), 119(6) 1269-75.*
Hcaplus Abstract, Accession No. 1997:208265, Kaneko, Furi Rajikaru no Rinsho (1995), 9, 116-123.*
Hcaplus Abstract, Accession No. 1996:628073, Kitajima et al., Japanese Patent No. 08208464 (1996).*
Hcaplus Abstract, Accession No. 1988:509240, Kawamur et al., Ganryu Aminosan (1987), 10(1), 99-107.*
Database CAPLUS on STN, American Chemical Society (ACS), Columbus, OH, USA), DN. 122:305890 & Salabert-Salvador, M.T. et al., QSAR relations from molecular connectivity of various physicochemical and pharmacological properties of a group of hypolipemic drugs, Ars Pharm., 1992, 33 (1-4, vol. 2), pp. 1086 to 1090.
Sulfur Amino Acids, vol. 7, No. 1, 201-205 (1984).
Geriat., Med., vol. 19, No. 3, 415-422 (1981).
Grundy, Medical Intelligence, Drug Therapy, "HMG-CoA Reductase Inhibitors for Treatment of Hypercholesterolemia", *New England Journal of Medicine*, vol. 319, No. 1, Jul. 7, 1988, pp 24-33.
Modern Physician, vol. 18, No. 1, 53-56 and 69-71 (1998).
Lin, Jin-Xiu, et al., "The Effect of Pravachol, Inositoli, Nicotinatis and Combining Treatment on Blood Lipid in Patients with Hyperlipidemia," *Chin. J. Arterioscler.*, 1997, pp. 227-230, 5(3); (and English Language Translation).

* cited by examiner

*Primary Examiner*—Raymond J. Henley, III
(74) *Attorney, Agent, or Firm*—Frishauf, Holtz, Goodman & Chick, P.C.

(57) ABSTRACT

Compositions having excellent blood lipid peroxide lowering activity are provided. In particular, compositions for lowering lipid peroxides in the blood which contain pravastatin together with at least one substance selected from the group consisting of taurine, pantethine and inositol hexanicotinate. Use of these compositions enables the provision of excellent preventive or remedial agents capable of lowering the concentration of lipid peroxides in the blood which show effects of injuring vascular endothelial cells, accelerating platelet aggregation, forming foam cells, etc.

21 Claims, No Drawings

LIPID PEROXIDE-LOWERING COMPOSITIONS

This is a Continuation-in-Part application of International Application No. PCT/JP01/09662 filed Nov. 5, 2001 which is incorporated herein by reference in its entirety.

BACKGROUND OF THE INVENTION

The present invention relates to blood lipid peroxide-lowering compositions consisting of pravastatin in combination with one or more substances selected from taurine, pantethine and inositol hexanicotinate.

An increase in blood lipid peroxide levels causes damage to endothelial cells, enhances platelet aggregation, and promotes foam cell forming, all of which contribute to arteriosclerosis. Thus lipid peroxide-lowering agents are considered to be useful agents.

Pravastatin reduces total cholesterol levels in the blood by inhibiting HMG-CoA reductase activity. However, it is not known that pravastatin reduces lipid peroxide levels in the blood.

Taurine and pantethine are known to reduce lipid peroxide levels in the blood (Reference: Sulfur Amino Acids, Vol. 7, No.1, 1984, p. 201–205; Geriatr. Med., Vol. 19, No. 3, p. 415–422).

However, it is not known that inositol hexanicotinate decreases lipid peroxide levels in the blood.

BRIEF DESCRIPTION OF THE INVENTION

The present invention relates to drug compositions containing pravastatin in combination with one or more substances selected from taurine, pantethine and inositol hexanicotinate, which reduce levels of lipid peroxides in the blood.

The present inventors investigated drug compositions that decrease lipid peroxide levels in the blood, and found that co-administration of pravastatin with taurine, pantethine or inositol hexanicotinate all decrease lipid peroxide levels in the blood and completed the present invention.

DETAILED DESCRIPTION OF THE INVENTION

Pravastatin (chemical name: (+)-(3R,5R)-3,5-dihydroxy-7-[(1S,2S,6S,8S,8aR)-6-hydroxy-2-methyl-8-[(S)-2-methylbutyryloxy]-1,2,6,7,8,8a-hexahydro-1-naphthyl]heptanoate) is a compound represented by the following chemical structure. It may exist in the form of a salt (particularly a sodium salt). The manufacturing methods of pravastatin have been disclosed in Japanese Patent Kokai Application No. SHO 57-2240 and so forth. Since pravastatin is commercially available, it is easily acquired.

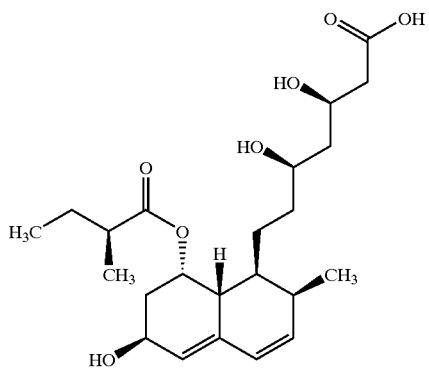

Blood lipid peroxides are lipid peroxides present in the blood, and involve hyperoxidated LDL (low-density lipoproteins) and so on.

The term "lowering" in the expression lipid peroxide-lowering agents indicates that the levels are decreased by clinically significant amounts following administration of the agents.

The weight percent of pravastatin contained in a tablet of the present invention of the lipid peroxide-lowering composition drug is 0.01 to 5%, preferably 0.05 to 3.0%. The weight percent of taurine in the tablet is typically 0.3 to 50%, preferably 1 to 25%. The weight percent of pantethine in the tablet is typically 1.3 to 50%, preferably 2.7 to 20%. The weight percent of inositol hexanicotinate in the tablet is typically 0.05 to 50%, preferably 0.5 to 25%.

The content of pravastatin contained in liquid and solution preparations of lipid peroxide-lowering composition according to the present invention is typically 1 to 100 mg/mL and preferably 3 to 7 mg/mL; that of taurine is typically 2.5–50 mg/mL, preferably 8 to 35 mg/mL. In addition, the content of pantethine in the liquid and solution preparation is typically 1 to 200 mg/mL, preferably 5 to 100 mg/mL, and that of inositol hexanicotinate typically 1 to 40 mg/mL, preferably 2 to 20 mg/mL.

Practical preparations of the drug compositions to reduce lipid peroxide levels in the blood are tablets, granules (involving powders), capsules, and liquids and solutions, etc., and they are manufactured following addition of the required additive agents or materials, if necessary, according to conventional methods described in The Pharmacopeia of Japan.

In the preparations described above, additive agents that are conventionally used can be employed based on the preparation.

For instance, in the case of tablets, lactose and crystalline cellulose are used as diluents, magnesium aluminometasilicate, etc., are used as stabilizing agents, hydroxypropylcellulose, etc., are used as binders, and magnesium stearate is used as a lubricant.

In granules and capsules, lactate and purified sucrose are used as diluents, magnesium aluminometasilicate is used as a stabilizing agent, corn starch, etc., are used as adsorbents, and hydroxypropylcellulose and polysorbate, etc., are used as binders.

In liquids and solutions, D-sorbitol solution and honey, etc., are used as sweeteners, dl-malic acid, etc., are used as flavoring agents, disodium dihydrogen ethylenediamine tetraacetate, etc., are used as stabilizing agents, ethanol is used as a co-solvent, and polyoxyethylene hydrogenated castor oil stearate 60, etc., are used as a solubilizer.

In the preparations described above, disintegrators such as crospovidone, etc.; adsorbents such as calcium silicate, etc.; coloring agents such as red ferric oxide, caramel, etc.; pH modifiers such as sodium benzoate, etc.; and a flavor may be used, if necessary.

EXAMPLES

The present invention is described in more detail by way of the following examples. However, the present invention is not limited to these examples.

Test Example 1

Tablets (1)

TABLE 1

|  | Taurine 4 tablets (680 mg) | Pantethine 4 tablets (1,440 mg) | Inositol hexanicotinate 4 tablets (1,400 mg) |
|---|---|---|---|
| Pravastatin sodium | 20 mg | 20 mg | 20 mg |
| Taurine | 500 mg | — | — |
| Pantethine | — | 500 mg | — |
| Inositol hexanicotinate | — | — | 500 mg |
| Crystalline cellulose | 120 mg | 12 mg | 12 mg |
| Magnesium aluminometasilicate | 144 mg | — | — |
| Sucrose esters of fatty acids | — | 140 mg | 140 mg |
| Hydroxypropylcellulose | 96 mg | 48 mg | 96 mg |
| Magnesium stearate | 24 mg | 24 mg | 24 mg |
| Crospovidone | 100 mg | 48 mg | 100 mg |
| Lactose | a | a | a | a: appropriate quantity (2) Manufacturing Methods

The amount of each component described above is weighed and prepared according to the methods described in the "General Rules for Preparations of Tablets" in "The Pharmacopeia of Japan".

(1) Composition

TABLE 2

|  | Taurine 4 packages (4 g) | Pantethine 4 packages (5.2 g) | Inositol hexanicotinate 4 packages (5 g) |
|---|---|---|---|
| Pravastatin sodium | 20 mg | 20 mg | 20 mg |
| Taurine | 500 mg | — | — |
| Pantethine | — | 1,000 mg | — |
| Inositol hexanicotinate | — | — | 1,000 mg |
| Purified sucrose | 1,400 mg | 1,600 mg | 1,400 mg |
| Stevia extracts | — | 16 mg | 16 mg |
| Corn starch | 1,200 mg | 1,200 mg | 1,200 mg |
| Polysorbate 80 | 80 mg | 48 mg | 80 mg |
| Magnesium aluminometasilicate | 144 mg | — | 144 mg |
| Magnesium stearate | 24 mg | 24 mg | 24 mg |
| Lactose | a | a | a | a: appropriate quantity

2) Manufacturing Methods

The amount of each component described above is weighed and prepared according to the methods described in the "General Rules for Preparations of Granules" in "The Pharmacopeia of Japan".

Test Example 3

Capsules (1) Components

TABLE 3

|  | Taurine 4 capsules | Pantethine 8 capsules | Inositol hexanicotinate 8 capsules |
|---|---|---|---|
| Pravastatin sodium | 20 mg | 20 mg | 20 mg |
| Taurine | 500 mg | — | — |
| Pantethine | — | 500 mg | — |
| Inositol hexanicotinate | — | — | 500 mg |
| Corn starch | 960 mg | 960 mg | 960 mg |
| Polysorbate 80 | 80 mg | 48 mg | 80 mg |
| Magnesium aluminometasilicate | 144 mg | — | 144 mg |
| Magnesium stearate | 24 mg | 24 mg | 24 mg |
| Lactose | a | a | a |
| Subtotal | 1,520 mg | 1,940 mg | 2,000 mg |
| Capsule | 320 mg | 640 mg | 640 mg |
| Total | 1,840 mg | 2580 mg | 2,640 mg | a: appropriate quantity (2) Manufacturing Methods

The amount of each component described above is weighed and prepared according to the methods described in the "General Rules for Preparations of Granules" in "The Pharmacopeia of Japan", and hard capsules are prepared by filling the granules into capsules.

Test Example 4

Liquids and Solutioins (1) Components

TABLE 4

|  | Taurine 100 mL | Pantethine 100 mL | Inositol Hexanicotinate 100 mL |
|---|---|---|---|
| Pravastatin sodium | 20 mg | 20 mg | 20 mg |
| Taurine | 500 mg | — | — |
| Pantethine | — | 500 mg | — |
| Inositol hexanicotinate | — | — | 500 mg |
| D-Sorbitol solution (70%) | 4 g | 6 g | 4 g |
| Honey | 7 g | 8 g | 7 g |
| dl-Malic acid | 200 mg | — | 200 mg |
| Disodium dihydrogen-ethylenediamine tetraacetate | 20 mg | 20 mg | 20 mg |
| Ethanol | 2 mL | 2 mL | 2 mL |
| Polyoxyethylene hydrogenated-castor oil stearate 60 | 100 mg | 100 mg | 100 mg |
| Sodium benzoate | 60 mg | 60 mg | 60 mg |
| Flavor | b | b | b |
| Distilled water | a | a | a | a: appropriate quantity,
b: trace amount (2) Manufacturing Methods

The amount of each component described above is weighed and prepared according to the methods described in the "General Rules for Preparations of Liquids and Solutions" in "The Pharmacopeia of Japan".

Test Examples (1) Test Compounds

Pravastatin with a purity of 99.4%, manufactured at Sankyo Co., Ltd. was used.

Taurine, pantethine and inositol hexanicotinate were purchased from Nacalai Tesque, Inc., Dai-ich Pharmaceutical Co., Ltd., and SHIRATORI PHARMACEUTICAL CO., LTD., respectively and were used.

(2) Test Animals

Beagle dogs aged 5 months were purchased from Covance Research Products Inc. and used after 1 month of quarantine and acclimatisation breeding.

(3) Form of the Preparation for Administration, Method of Preparation of the Formulation and Method of Stocking the Formulation The required amounts of pravastatin or each component of the combination drug calculated from the body weight of each dog were weighed and filled in a gelatin capsule purchased from TORPAC Inc. Capsules filled with pravastatin were stocked in a refrigerator and those filled with combination drugs stocked at room temperature until use.

The combination drugs were filled in identical gelatin capsules.

(4) Route of Administration and Administration Period

Pravastatin or combination drug capsules were forcibly orally administered to each of the test animals once daily between 9:00 and 12:30. Animals were fasted for 2 or 3 hr prior to administration of the capsules.

The administration period was 11 successive days.

(5) Preparation of Test Samples and Procedures

Blood (10 mL) was collected from the superficial radial vein 3 or 4 days prior to administration (−3 or −4 days in the first week prior to capsule administration) and 4 and 8 days after administration of the capsule. Animals were fasted for approximately 18 hr prior to blood collection. Collected blood was placed in a test tube and left at room temperature for 0.5–1 hr and centrifuged (3,000 rpm, for 10 min). The obtained serum was used for assays of blood lipid peroxides according to Yagi's methods.

A fluorometer (Hitachi, Ltd., F3000) was used for assay of the lipid peroxides.

Results

Lipid peroxide levels in blood collected from dogs treated with pravastatin or one compound selected from taurine, pantethine and inositol hexanicotinate, as well as combinations of pravastatin together with one of the above drugs, were converted to their relative ratios against their averaged pre-dosing levels (100 as determined 2 and 1 weeks prior to drug administration). The averaged value in each group was obtained from 5 animals a group.

TABLE 5

(Effects of co-administration of pravastatin and taurine)

| Test Substance | Dose (mg/kg) | Blood Lipid Peroxide Levels after administration | |
|---|---|---|---|
| | | 4 days | 8 days |
| Pravastatin alone | 2 | 110.8 | 116.2 |
| Taurine alone | 1,000 | 95.8 | 93.8 |
| Pravastatin + taurine | 2 1,000 | 89.9 | 77.5 |

TABLE 6

(Effects of co-administration of pravastatin and pantethine)

| Test Substance | Dose (mg/kg) | Blood Lipid Peroxide Levels after administration | |
|---|---|---|---|
| | | 4 days | 8 days |
| Pravastatin alone | 2 | 110.8 | 116.2 |
| Pantethine alone | 300 | 82.5 | 105.0 |
| Pravastatin + pantethine | 2 300 | 83.6 | 75.4 |

TABLE 7

(Effects of co-administration of pravastatin and inositol hexanicotinate)

| Test Substance | Dose (mg/kg) | Blood Lipid Peroxide Levels after administration | |
|---|---|---|---|
| | | 4 days | 8 days |
| Pravastatin alone | 2 | 110.8 | 116.2 |
| Inositol hexanicotinate alone | 400 | 98.5 | 96.5 |
| Pravastatin + inositol hexanicotinate | 2 400 | 83.8 | 81.3 |

The composition of the present invention can be used for lowering blood lipid peroxide levels in a mammal and in particular a human. When administering to a human (or other mammal) in need of treatment, an effective amount of an agent which is pravastatin in combination with one or more of taurine, pantethine and inositol hexanicotinate, is used.

Although the dose of compounds used according to the invention may widely vary depending on the extent of diseases and age of patients, (e.g. human patients), the dose of one administration of pravastatin is normally within the range of from 0.01 mg/kg to 10 mg/kg, preferably from 0.1 mg/kg to 1 mg/kg, administered once or several times a day dependent on the extent of diseases.

The dose of one administration of taurine is normally within the range of from 1 mg/kg to 600 mg/kg, preferably from 10 mg/kg to 60 mg/kg, administered once or several times a day dependent on the extent of diseases.

The dose of one administration of pantethine is normally within the range of from 0.06 mg/kg to 120 mg/kg, preferably from 0.6 mg/kg to 12 mg/kg, administered once or several times a day dependent on the extent of diseases.

The dose of one administration of inositol hexanicotinate is normally within the range of from 0.16 mg/kg to 36 mg/kg, preferably from 1.6 mg/kg to 3.6 mg/kg, administered once or several times a day dependent on the extent of diseases.

The present invention, drug compositions of pravastatin in combination with a drug selected from taurine, pantethine and inositol hexanicotinate, exert excellent blood lipid peroxide-lowering effects.

What is claimed is:

1. A pharmaceutical composition for lowering lipid peroxides in the blood, said composition comprising a pharmaceutically acceptable additive agent in admixture with pravastatin or its pharmaceutically acceptable salt and one or more compounds selected from the group (a) consisting of taurine and pantethine, in amounts to form a synergistically effective mixture to lower blood lipid peroxide levels.

2. The pharmaceutical composition of claim 1 in solid dosage form containing 0.01 to 5% pravastatin or its pharmaceutically acceptable salt; and one or more of the compounds selected from group (a) in the following amounts 0.3 to 50 wt. % taurine and 1.3 to 50 wt. % pantethine.

3. The pharmaceutical composition of claim 2, wherein the compound selected from group (a) is taurine.

4. The pharmaceutical composition of claim 2, wherein the compound selected from group (a) is pantethine.

5. The pharmaceutical composition of claim 2, containing 0.05 to 0.03 wt. % pravastatin.

6. The pharmaceutical composition of claim 5, wherein the compound selected from group (a) is taurine in an amount of 1 to 25 wt. %.

7. The pharmaceutical composition of claim 5, wherein the compound selected from group (a) is pantethine in an amount of 2.7 to 20%.

8. The pharmaceutical composition of claim 1 in liquid form containing 1 to 100 mg/ml pravastatin or its pharmaceutically acceptable salt; and one or more compounds selected from group (a) in the following amounts 2.5 to 50 mg/ml taurine and 1 to 200 mg/ml pantethine.

9. The pharmaceutical composition of claim 8, wherein the compound selected from group (a) is taurine.

10. The pharmaceutical composition of claim 8, wherein the compound selected from group (a) is pantethine.

11. The pharmaceutical composition of claim 8, containing 0.05 to 0.03 wt. % pravastatin.

12. The pharmaceutical composition of claim 11, wherein the compound selected from group (a) is taurine in an amount of 1 to 25 wt. %.

13. The pharmaceutical composition of claim 11, wherein the compound selected from group (a) is pantethine in an amount of 2.7 to 20%.

14. A kit comprising a plurality of separate containers, wherein at least one container contains pravastatin and at least one different container contains one or more compounds selected from the group (a) consisting of taurine and pantethine, wherein said kit comprises an amount of pravastatin and said one or more compounds that is synergistically effective for lowering blood lipid peroxide levels in a human.

15. The kit of claim 14, wherein the selected compound of group (a) is taurine.

16. The kit of claim 14, wherein the selected compound of group (a) is pantethine.

17. A method of lowering blood lipid peroxide levels in a human, comprising administering to a human in need thereof a synergistically effective amount to lower said blood lipid peroxide levels of an agent comprising pravastatin in combination with one or more compounds selected from the group (a) consisting of taurine and pantethine.

18. The method of claim 17, wherein the selected compound of group (a) is taurine.

19. The method of claim 17, wherein the selected compound of group (a) is pantethine.

20. The method of claim 17 wherein the agent is in solid dosage form containing 0.01 to 5% pravastatin or its pharmaceutically acceptable salt; and one or more of the compounds selected from group (a) in the following amounts 0.3 to 50 wt. % taurine and 1.3 to 50 wt. % pantethine.

21. The method of claim 17 wherein the agent is in liquid form containing 1 to 100 mg/ml pravastatin or its pharmaceutically acceptable salt; and one or more compounds selected from group (a) in the following amounts 2.5 to 50 mg/ml taurine and 1 to 200 mg/ml pantethine.

* * * * *

UNITED STATES PATENT AND TRADEMARK OFFICE
CERTIFICATE OF CORRECTION

PATENT NO. : 6,998,422 B2
APPLICATION NO. : 10/428394
DATED : February 14, 2006
INVENTOR(S) : Ohsawa et al.

It is certified that error appears in the above-identified patent and that said Letters Patent is hereby corrected as shown below:

Title Page, Left Column, Item (30) Foreign Application Priority Data, insert -- Nov. 7, 2000 (JP) ...... 2000-339457 --.

Column 3, line 6, after "(1)" insert -- Composition --.

Signed and Sealed this

Thirteenth Day of March, 2007

JON W. DUDAS
*Director of the United States Patent and Trademark Office*